(12) United States Patent
Laluet et al.

(10) Patent No.: US 10,012,362 B2
(45) Date of Patent: *Jul. 3, 2018

(54) GLASS-CERAMIC ARTICLE COMPRISING A LUMINOUS COLOR DISPLAY

(71) Applicant: EUROKERA S.N.C., Chateau-Thierry (FR)

(72) Inventors: Jean-Yves Laluet, Paris (FR); Pierrick Guiset, Massy (FR); Gaelle Ferriz, Reims (FR); Claire Mallet, Paris (FR)

(73) Assignee: EUROKERA S.N.C., Château-Thierry (FR)

( * ) Notice: Subject to any disclaimer, the term of this patent is extended or adjusted under 35 U.S.C. 154(b) by 672 days.

This patent is subject to a terminal disclaimer.

(21) Appl. No.: 14/421,678

(22) PCT Filed: Aug. 12, 2013

(86) PCT No.: PCT/FR2013/051925
§ 371 (c)(1),
(2) Date: Feb. 13, 2015

(87) PCT Pub. No.: WO2014/027161
PCT Pub. Date: Feb. 20, 2014

(65) Prior Publication Data
US 2015/0219312 A1 Aug. 6, 2015

(30) Foreign Application Priority Data
Aug. 14, 2012 (FR) ..................... 12 57797

(51) Int. Cl.
| | |
|---|---|
| *F21V 9/30* | (2018.01) |
| *F21V 9/16* | (2006.01) |
| *C03C 10/00* | (2006.01) |
| *C03C 17/00* | (2006.01) |
| *C03C 17/34* | (2006.01) |
| *F24C 7/08* | (2006.01) |
| *F21K 9/90* | (2016.01) |
| *G01N 21/31* | (2006.01) |
| *F24C 15/10* | (2006.01) |
| *G02B 5/22* | (2006.01) |

(52) U.S. Cl.
CPC ............... *F21V 9/16* (2013.01); *C03C 10/00* (2013.01); *C03C 17/002* (2013.01); *C03C 17/007* (2013.01); *C03C 17/34* (2013.01); *F21K 9/90* (2013.01); *F24C 7/083* (2013.01); *F24C 15/102* (2013.01); *G01N 21/31* (2013.01); *C03C 2217/485* (2013.01); *G02B 5/223* (2013.01)

(58) Field of Classification Search
CPC ............... C03C 17/002; C03C 17/007; C03C 2217/485; F21C 7/082; F21V 9/10; F24C 15/102; G09F 23/0058; G09F 9/33; H03K 17/941; H05B 3/746; H05B 6/1209; H05B 6/1218
See application file for complete search history.

(56) References Cited

U.S. PATENT DOCUMENTS

| | | |
|---|---|---|
| 2012/0295081 A1 | 11/2012 | Henze et al. |
| 2013/0040116 A1 | 2/2013 | Henze et al. |
| 2013/0070451 A1* | 3/2013 | Mulet ................. F21V 1/02 362/231 |
| 2013/0098903 A1 | 4/2013 | Di Giovanni et al. |
| 2013/0183487 A1 | 7/2013 | Henze et al. |
| 2013/0286630 A1 | 10/2013 | Guiset et al. |
| 2014/0146530 A1 | 5/2014 | Guiset et al. |

FOREIGN PATENT DOCUMENTS

| | | |
|---|---|---|
| DE | 103 09 225 A1 | 9/2004 |
| DE | 10 2010 004 741 A1 | 7/2011 |
| WO | WO 2011/089327 A1 | 7/2011 |
| WO | WO 2012/001300 A1 | 1/2012 |
| WO | WO 2012/168011 A1 | 12/2012 |
| WO | WO 2012/172257 A1 | 12/2012 |

OTHER PUBLICATIONS

U.S. Appl. No. 14/442,619, filed May 13, 2015, Laluet, et al.
International Search Report dated Oct. 22, 2013 in PCT/FR2013/051925 Filed Aug. 12, 2013.

* cited by examiner

*Primary Examiner* — Robert May
*Assistant Examiner* — Leah S Macchiarolo
(74) *Attorney, Agent, or Firm* — Oblon, McClelland, Maier & Neustadt, L.L.P.

(57) ABSTRACT

The present invention relates to an article having at least one colored luminous region, in particular a display, said article comprising at least one glass-ceramic substrate having a luminous transmission ranging from 0.8% to 40% and an optical transmission of at least 0.1% for at least one wavelength in the range extending from 420 to 780 nm, at least one light source and at least one inkjet filter of thickness comprised between 1 and 50 μm, so as to form at least one colored luminous region, in particular a display, in at least one region of the glass-ceramic substrate.

23 Claims, No Drawings

GLASS-CERAMIC ARTICLE COMPRISING A LUMINOUS COLOR DISPLAY

The present invention relates to the field of glass-ceramics. More precisely, it relates to an article (or product) made of glass-ceramic, and especially to a glass-ceramic plate, intended in particular to cover or contain heating elements, said article being provided with a luminous color display (or at least one colored luminous region) in at least one chosen region of the article.

Sales of articles such as cooktops made of glass-ceramic have been increasing constantly for several years. This success is especially explained by the attractive appearance of these plates and because they are easy to clean.

It will be recalled that glass-ceramic is initially glass, this glass being called the precursor glass (or green glass), the specific chemical composition of which allows, via suitable heat treatments called ceramization treatments, controlled crystallization of the glass. This specific, partially crystallized structure provides the glass-ceramic with unique properties.

Various types of glass-ceramic plates currently exist, each variant being the result of major studies and many trials, being given that it is very difficult to make modifications to these plates and/or to the process used to obtain them without running the risk of adversely affecting the desired properties: in order to be employed as a cooktop, a glass-ceramic plate must in general have a transmission in the visible wavelength range that is both sufficiently low to at least partially hide the underlying heating elements when turned off and sufficiently high that, depending on the case (radiant heating, induction heating, etc), the user can see whether the heating elements are turned on—for the sake of safety. The glass-ceramic plate must also have a high transmission at wavelengths in the infrared range, especially in the case of radiant heaters.

Most plates are currently dark, especially black, in color, this color being obtained for example by adding vanadium oxide to the batch materials of the green glass before it is melted, this oxide providing, after ceramization, a strong orange-brown color associated with reduction of the vanadium. Other coloring agents, such as cobalt oxide and manganese oxide, may also be used. With a low transmission coefficient, below 600 nm, these plates especially allow red elements, such as hot heating elements or indeed luminous displays based on monochromatic red light-emitting diodes, to be seen. More transparent glass-ceramic plates (such as the glass-ceramics KeraVision or KeraResin, sold by EuroKera) also exist and allow other "pure" colors (colors produced by monochromatic diodes), such as blue and green, to be displayed.

However, recently it has become necessary to display a greater variety of information with a greater variety of colors, in particular synthetic colors produced by mixing a number of wavelengths (the case for the color white). Since the transmission coefficient of glass-ceramic plates is not uniform over the entire visible spectrum, the relative amplitudes of the various (spectral) components of the transmitted light are however generally modified, the color after transmission possibly being very different to that produced by the source.

In particular, technologies based on light-emitting diodes (LEDs), commonly employed to produce white light (for example using a source of blue light covered with a phosphor that absorbs some of said light and reemits yellow light), cannot be used to produce a white color through a glass-ceramic. While the balance between the blue and yellow light is initially such that mixing them provides the viewer with the impression of white light, since this light passes through the glass-ceramic, which does not absorb uniformly (the blue is strongly absorbed and the yellow less so), the viewer does not perceive the color white through the glass-ceramic but sees, for example, the color pink, orange or red.

Likewise, the use of LEDs producing polychromatic emissions (for example formed from three monochromatic sources the intensities of which are set independently, such as "RGB" LEDs, which use three sources, i.e. a red, green and blue source) in order to produce white light, for example, is not appropriate since the nonuniform absorption of the glass-ceramic in the visible domain shifts the balance between the colors, and also produces a pink, orange, or red rendering. The respective brightness of the RGB components can be adjusted, but the mixing must be perfect (especially in space—good overlap of the light beams—and in time—same phase, especially if the beams are to be amplitude modulated) if nonuniformities are to be avoided. The distance separating the three emitting regions is often the cause of poor mixing, leading to a nonuniform color. Likewise, the three R, G and B chips are subject to temperature drift and they age at different rates, leading to nonuniformities in color appearing over time. Furthermore, depending on the manufacturing batch of the red, green and blue LEDs, the color of the RGB LEDs varies from one LED to another. RGB LEDs are also more bulky than the LEDs commonly used in display units, and are more difficult to incorporate into a control panel.

For these reasons, white displays, or displays in most colors other than red, in particular in synthetic colors, are not used with glass-ceramics, especially dark or colored glass-ceramics, due to their nonuniform absorption over the visible range since any nonmonochromatic light passing through them sees its color modified, and the wider the spectrum is the more critical this becomes, as in the case of white sources.

The aim of the present invention is therefore to provide new and improved glass-ceramic articles (such as plates) and in particular to provide new glass-ceramic articles with luminous displays in a more varied range of colors, especially colors other than red, and in particular white, this display not having the drawbacks mentioned above, providing a wide range of precise colors and being particularly suitable for application to dark-colored and/or very absorbent plates and/or plates that are themselves colored. More particularly, the present invention seeks to provide a solution suitable for or easily applicable to any type of glass-ceramic (whether smooth, embossed or containing bumps, whether clear or dark, whether colored or not, etc), this solution allowing one or more regions of chosen color(s) to be obtained, the colors obtained being uniform, this solution furthermore being simple to implement and compatible with the glass-ceramic manufacturing process and the constraints on their use.

This objective is achieved by the new article according to the invention, the article having at least one colored (in the wider sense, also including white) luminous region (in particular a display), said article comprising at least one glass-ceramic substrate (in particular a plate intended for example to cover or contain at least one heating element) having a luminous transmission ranging from 0.8% to 40% and an optical transmission of at least 0.1% for at least one wavelength in the range extending from 420 to 780 nm (located in the visible range), at least one light source (and/or a display unit incorporating said source) and at least one inkjet filter of thickness comprised between 1 and 50 µm (coupled (in operation) to said source (and likewise to the plate, the colored region obtained especially resulting from (the action/effect of) these three components)) so as to form, in particular, at least one colored luminous region, in particular a display (display of information/symbols or decorative patterns for example), in at least one region of the glass-ceramic substrate. As explained above, this filter may especially be combined (in terms of position) with the source and/or with the glass-ceramic substrate and/or with an intermediate element (for example an extracting means), and is preferably securely fastened to the glass-ceramic substrate.

The term "inkjet filter" is understood to mean an optical filter (acting on the transmission of the light), in particular a color filter (the filter affecting light transmission as a function of wavelength) printed (or applied) by inkjet (or obtained by inkjet printing), this filter especially taking the form of a film or layer, in particular being based on at least one ink (possibly comprising one or more organic and/or inorganic and/or mineral materials), and being (semi)transparent (especially in the sense that it is transparent at certain wavelengths in the visible and not transparent to/opaque/it affects other wavelengths, this filter furthermore generally having a luminous transmission of at least 5%, especially at least 20%, and in particular at least 30%), in particular allowing certain wavelengths in the visible spectrum to be absorbed and/or reflected and/or reemitted. It is particularly advantageous for the filter to be an absorption filter (the filter affecting the transmission of the light by absorbing certain wavelengths, the light absorbed possibly, in particular, being converted to heat and/or emitted at other wavelengths). It may be applied to or printed on the glass-ceramic substrate and/or to/on at least one light source and/or to/on and intermediate element, as explained below. At least one light source is coupled (in operation) to at least one such corrective filter (i.e. the light it emits passes through said filter) in order to produce the desired display through the glass-ceramic substrate with which this assembly is combined.

The aforementioned filter is chosen depending on (or is specific to, or as a function of) the glass-ceramic (i.e. on the optical transmission—or spectral transmission or dispersion—of the glass-ceramic substrate, the optical/spectral transmission itself depending on the composition and the thickness of said substrate) and possibly on the light source, as explained below, so as to form at least one colored luminous region with set color coordinates, in particular a colored region having a color other than red, and especially a white colored region or a color region of a synthetic color obtained by mixing a number of wavelengths.

The present invention has demonstrated that selecting glass-ceramics, which, although possibly dark, have luminous and optical transmissions according to the invention, and combining them with filters selected as required, as mentioned above, in order to compensate or correct, in a controlled way, the spectral dispersion of the glass-ceramic, allows the desired color rendering to be obtained whatever the initial spectrum of the light source viewed through said glass-ceramic, without limiting the choice of light sources or requiring complicated conversion procedures to be performed on said sources or the glass-ceramic. Moreover, the present invention has demonstrated that using inkjet filters of thickness comprised between 1 and 50 µm allows the improved glass-ceramic articles sought to be obtained with advantages, and without the defects or drawbacks possibly observed with other types of filters.

The filter, chosen depending on the glass-ceramic and possibly the source (depending on the intended objective, as explained below), allows the desired transmission to be obtained from the filter/glass-ceramic assembly (the color being corrected or a neutral transmission, i.e. a transmission that does not alter the initial color of the source, being obtained). The invention is especially suitable for dark or colored glass-ceramic plates meeting the transmission criteria, the invention controlling the color function of their display(s). The invention enables, for a given color source, a given target color to be obtained, and in particular displays/display units to be produced that are optionally identical in color to the initial color, especially white display units or display units of colors previously not used with glass-ceramics. The invention also makes it possible to produce regions of different colors over one glass-ceramic, by associating particular colors with different spaces or functions, for example.

The invention applies, with the same advantages, both to flat glass-ceramic substrates and to glass-ceramic substrates having surfaces that are not flat or that contain irregularities, for example glass-ceramic plates having bumps on their lower face, the inkjet filter according to the invention being able to closely follow the irregular surface in question with a constant thickness, in contrast to other types of filter and/or filters deposited with greater thicknesses.

For example, it turns out that filters taking the form of one or more polymer sheets are not able to precisely follow the surface of the bumps, leaving empty spaces between the latter and the sheet(s), this leading to reflections, from between the glass-ceramic and the filter, that differ depending on whether they occur with the bumps or between the latter. The path followed by the light is thus not uniform over the entire region equipped with the filter. Choosing to deposit a filter by screen printing allows these voids, and the resulting reflections, to be avoided, but in contrast results in a filter that is thicker between the bumps than at the peaks of the bumps. Thus, light does not pass through the same thickness of filter over the entire region in question, thereby leading, depending on the circumstances (white display, for example) to clear differences in the color obtained from bump peaks and bump troughs. Application by inkjet, according to the invention, advantageously allows these two drawbacks (reflections and nonuniform thickness) to be overcome, and a good uniformity to be obtained for the resulting color.

Moreover, as explained below, the inkjet filter may advantageously be formed from thermally resistant compositions that can withstand the temperatures to which the regions in question, of the articles according to the invention, are subjected, for example the temperatures to which control panels of glass-ceramic plates are exposed, in contrast to filters taking the form of polymer sheets; the latter, since they are less resistant to heat, must be placed a distance away from the glass-ceramic in order not to be degraded, thereby increasing how complicated it is to implement the filter. The solution according to the invention is particularly durable and simple to implement.

Furthermore, once the filter spectrum allowing the desired color to be obtained has been determined, as explained below, a polymer sheet (or combination of polymer sheets) having exactly this spectrum does not necessarily exist, meaning that it is necessary to choose the filter that most closely matches the target filter, thereby meaning that a large number of different filters must be kept in stock. Therefore, it is not possible to achieve a target color with as much precision as would be desired. With such polymer filters, it is in addition not possible to finely adapt the filter to variations in the transmission spectrum of the glass-ceramic due to natural variations in the manufacturing process, such as variations in composition and thickness.

As for choosing to deposit a filter by screen printing, it enables a better adjustment of the colors, via precise dosing of the amount of pigments used with this type of filter; however, the weight measurements introduce uncertainty, and this process entails the preparation of a particular solution for each manufacturing batch, depending on variations in the composition or thickness of the glass-ceramic.

In the present invention, adjustment of the colors is in contrast particularly simple and precise. In particular, the filter is defined by a ratio between various colors, generally primary colors (such as cyan, magenta and yellow), for example being defined by a ratio between the colors cyan, magenta, yellow and black, and is advantageously obtained by superposing depositions (of inks) of each of the colors in the ratios (or proportions) adopted. It is thus not necessary to prepare a solution with the correct ratios beforehand; the ratios are, for example, simply entered into the software program that controls the printer just before printing is initiated. They can therefore be very easily matched to the batches of glass-ceramics used (the thickness and composition of which vary due to natural variation in the manufacturing process) in order to obtain a constant resulting color with a given light source over various batches of glass-ceramics.

The article according to the invention may advantageously be a cooktop, but may also be any other article, made of a glass-ceramic, with a functional or decorative display, or even an article or module or assembly or system (primarily) acting as a (decorative and/or functional) display having at least one light source coupled to at least one corrective filter, this assembly being coupled to at least one glass-ceramic article, in particular a glass-ceramic plate, according to the invention.

The expressions "glass-ceramic articles" or "articles made of glass-ceramic" are understood to mean not only articles made of actual glass-ceramic but also articles made of any other analogous material suited to the same applications (for example glass whether reinforced or not), in particular any material able to withstand high temperatures and/or especially having a zero or almost zero thermal expansion coefficient (for example a thermal expansion coefficient of less than $1.5 \times 10^{-7}$ $K^{-1}$, as in the case of the glass-ceramic plates used with radiant heaters). However, the article is preferably made of actual glass-ceramic.

Preferably, the article (substrate) according to the invention is formed by a flat, or mainly or almost flat (in particular deviating from planarity along a diagonal by less than 0.1%, preferably by about 0%) glass-ceramic plate (generally of between 3 and 4 mm in thickness, especially about 4 mm in thickness), and it is intended to be used as a cooktop. Such a plate is generally intended to be incorporated in a stove or range comprising said plate and heating elements, for example radiant or halogen heaters or induction heating elements.

In use, the plate generally has an "upper" face (visible face), another "lower" face (often hidden in the chassis or casing of a range for example) and an edge face (or side face or thickness). The upper face is generally flat and smooth but may also comprise at least one protruding and/or recessed region and/or at least one aperture (for example if the plate includes an aperture intended for housing a gas burner). The lower face may especially be smooth or comprise bumps that increase its strength, obtained by rolling for example. As required, if bumps are used, an index resin may be applied to the lower surface in order to smooth it, if this is necessary.

The article according to the invention is advantageously based on any glass-ceramic that has an intrinsic luminous transmission ranging from 0.8% to 40% (in particular from 2.3 to 40%) and an intrinsic optical transmission (defined as is known by the ratio of the transmitted intensity to the incident intensity at a given wavelength) of at least 0.1% for at least one wavelength lying in the visible range above 420 nm (and up to 780 nm), and preferably of at least 0.1% for all wavelengths in the range extending from 420 to 780 nm. The term "intrinsic" is understood to mean that the plate possesses such transmission properties itself, uncoated. Luminous transmission ($T_L$) is measured according to standard ISO 9050:2003 (which also mentions optical transmission) under illuminant D65, and is the total transmission (especially integrated over the visible domain and weighted by the spectral sensitivity curve of the human eye) taking into account both direct transmission and possible diffuse transmission, the measurement being carried out, for example, using a spectrophotometer equipped with an integrating sphere, the measurement for a given thickness then being converted, if required, to a reference thickness of 4 mm according to standard ISO 9050:2003. The invention is applicable, in a particularly advantageous way, to dark plates, especially black or brown plates, meeting such transmission criteria, but the glass-ceramic used may also be a clear glass-ceramic meeting such criteria, the solution according to the invention allowing a luminous display of the precise desired color to be obtained, while being adaptable, with a high degree of flexibility, to all of this range of plates, simply and without running the risk of degrading other properties of the plates.

In a first embodiment, the glass-ceramic is in particular a dark glass-ceramic (especially such that the L* value in the CIE color system, calculated from the transmission spectrum of said glass-ceramic over the visible range, is lower than 70%) having a luminous transmission in the visible of 0.8% to 5%, in particular from 0.8 to 2.5% and having an optical transmission higher than 0.1% for at least one wavelength in the visible range above 450 nm.

In another advantageous embodiment, the glass-ceramic is of the lithium aluminosilicate type and has an intrinsic luminous transmission ranging from 2.3% to 40%, in particular higher than 2.5%, especially higher than 3.5%, and an intrinsic optical transmission of at least 0.6% for at least one wavelength in the range extending from 420 to 480 nm. In this case, whether the glass-ceramic is clear or dark, it preferably comprises at least one masking means intended to mask at least some of the associated underlying elements (especially heating means) if required, excluding the light-emitting devices/illuminated regions and if required radiation heating means, the filter(s) being in this case essentially used in the unmasked luminous regions.

In particular, advantageously, a glass-ceramic comprising the following constituents and/or obtained by ceramization of glass having the following composition is used, within the ranges below, expressed in percentages by weight: $SiO_2$: 52-75%; $Al_2O_3$: 18-27%; $Li_2O$: 2.5-5.5%; $K_2O$: 0-3%; $Na_2O$: 0-3%; $ZnO$: 0-3.5%; $MgO$: 0-3%; $CaO$: 0-2.5%; $BaO$: 0-3.5%; $SrO$: 0-2%; $TiO_2$: 1.2-5.5%; $ZrO_2$: 0-3%; $P_2O_5$: 0-8%, and preferably, within the ranges below, expressed in percentages by weight: $SiO_2$: 64-70%; $Al_2O_3$: 18-21%; $Li_2O$: 2.5-3.9%; $K_2O$: 0-1.0%; $Na_2O$: 0-1.0%; $ZnO$: 1.2-2.8%; $MgO$: 0.20-1.5%; $CaO$: 0-1%; $BaO$: 0-3%; $SrO$: 0-1.4%; $TiO_2$: 1.8-3.2%; $ZrO_2$: 1.0-2.5%.

The glass-ceramic may also comprise up to 1 wt % of nonessential constituents that do not affect melting of the green glass or the subsequent devitrification that results in the glass-ceramic. Coloring agents may especially be added to the composition in the case for example of black or brown glass-ceramics. For example, the composition of the plate may advantageously comprise vanadium oxide in an amount of between 0.01% and 0.2%, preferably 0.05% or less, even 0.04% or less. The amount of vanadium oxide used is preferably between 0.01 and 0.03%.

The glass-ceramic may also contain, so as to hide the heating elements, and optionally in combination with the vanadium oxide, the following other coloring agents (ranges by weight): $Fe_2O_3$: 0-0.2%, CoO: 0-1% and preferably 0-0.12%, and even NiO, CuO and/or MnO. The glass-ceramic may also comprise tin oxide (or other reducing agents such as metal sulfides) in an amount smaller than 0.5%, the tin oxide promoting the reduction of the vanadium during the ceramization step, especially causing color to appear.

The dark glass-ceramic preferred according to the invention generally comprises β-quartz crystal structures within a residual vitreous phase, and the absolute value of its thermal expansion coefficient is advantageously $15 \times 10^{-7}/°$ C. or less, even $5 \times 10^{-7}/°$ C. or less.

As defined above, the article according to the invention also comprises at least one light source, possibly a continuous or discontinuous source, and if required comprises a number of sources (their number and arrangement possibly being varied to make the illumination more uniform). The one or more sources may be integrated in/coupled to one or more display unit structures (for example to 7-segment light-emitting diodes or liquid crystals), to an electronic control panel with touch-sensitive controls and a digital display, etc. The light sources are preferably formed by light-emitting diodes (LEDs) that are spaced apart to a greater or lesser extent, the diodes possibly being associated with one or more waveguides as discussed below. Diodes are advantageously used in the present invention, especially because of their bulk, efficiency, durability and their ability to withstand the conditions (heat, etc) of their environment.

The diodes may be encapsulated, i.e. comprise a semiconductor component and a package (for example made of an epoxy or nylon resin) encapsulating the semiconductor component. The diodes may also be semiconductor chips without collimating lenses, for example being about one hundred μm or about one mm in size, optionally with minimal encapsulation (protective encapsulation for example).

The diodes may be borne by a support or strip or mounting, this mounting possibly having a treated (flat or sloped) surface and/or a surface that has been made reflective, so as to increase the luminous efficiency, for example, it may be coated with a lacquer or paint and/or a mirror layer and/or be coupled to a white or metallic reflector so as to better direct the emitted light.

The one or more sources may be joined (to the plate or to another constituent part of the article, such as the control panel for example) by soldering, clip-fastening, adhesive bonding, etc, and, if required, by way of another element. For example, the diodes, soldered to a support itself housed in a metal strip, may be fitted by clip-fastening or adhesive bonding of the strip. The positioning of the one or more sources (especially relative to the plate) is tailored to produce a display through the glass-ceramic.

The sources, and their power supply and control, may optionally be dissociated so as to allow simultaneous or separate illumination of the desired luminous regions as required. Each source may be a monochromatic (pure color) source, especially in the case where a number of monochromatic sources are combined (RGB LEDs for example) in order to emit a polychromatic spectrum (synthetic color), or may be a polychromatic source. The invention advantageously allows the nonuniform absorption, by the glass-ceramic, of the polychromatic spectrum of the one or more sources to be corrected (for example for a white LED), and is particularly applicable to articles employing polychromatic light sources (alone or in combination).

The expression "monochromatic light source" is understood to mean a light source having a single emission peak in the visible wavelength range, the peak width varying from 1 to 100 nm and preferably from 5 to 50 nm.

The expression "polychromatic light source" is understood to mean a light source that has at least two emission peaks at different wavelengths in the visible wavelength range. The color perceived (visually by the user) is then a mixture of the various wavelengths. It may be an LED, and/or an LED display unit, with an emission spectrum having a main emission peak and another emission peak, for example caused by fluorescence, which is wider than the main peak and generally less bright. The polychromatic LED will in particular emit a first (high or low brightness) emission at between 400 and 500 nm and a second (high or low brightness) emission in the visible above 500 nm (the case for example of LEDs formed by at least one light-emitting diode and one or more photoluminescent phosphors).

White LEDs may in particular be used as sources and they may for example be fabricated using a chip of a single-crystal semiconductor, such as indium gallium nitride (InGaN), emitting in the blue, the chip being covered with a transparent resin (such as silicone or epoxy resin) containing inorganic phosphors (for example YAG:Ce) that absorb in the blue and emit in the yellow. By way of examples of other advantageous polychromatic LEDs, mention may especially be made of the following LEDs or display units: the XLamp® LED or High Brightness LED range from CREE; the Nichia Helios, Nichia Rigel, LED lamps NSSM, NSSW, NSEW, NS9 and NS2 from Nichia; the white TOPLED® series and the LW Q38E, LW L283 and LW Q38G from OSRAM; the Luxeon® Rebel White and Luxeon® K2 range from Philips Lumileds; the LEDs referenced E1S19, E1S27, E1S62, E1S66, E1S67, E1SAG, E1SAP, EASAA, EASAU, EASAV, E1L4x and E1L5x from Toyoda Gosei; the LEDs referenced HSMW-C120, HSMW-C130, HSMW-C191, HSMW-C197 and HSMW-C265 from Avago Technologies; the LEDs referenced LTW-C193TS5 and LTW-C191TS5 from LITE-ON; the LEDs referenced WH104L-H, WH104-NZ and WH107 from Seoul Semiconductor; the LED referenced 19-213/T1D-KS1T1B2/3T from Everlight, etc.

Mention may also be made of the following LED-comprising display units: the 7-segment white display units referenced HDSM-431W and HDSM-433W from Avago Technologies, or referenced FN1-0391W010JBW and FN1-0391W050JBW from FORGE EUROPA; the Dot Matrix® displays from KingBright e.g. referenced TA20-11YWA; and the Bar Graph Array® displays from KingBright, for example referenced DC10YWA. It will be noted that LED-comprising display units are luminous display devices the "primary" light source of which consists of one or more LEDs. These devices generally comprise luminous "segments" (for example 7-segment display units), dots (matrix display units) or bars, one segment generally being formed by a reflector, the one or more LEDs generally being inserted at one end of the reflector and the light being guided to the other (visible) end, the internal walls of the reflector possibly scattering light and/or the visible end of the segment possibly being covered with a highly transparent plastic material.

As mentioned above, the article may comprise, in addition to the one or more sources, at least one waveguide intended to guide light from one part of the article to another (in particular by total internal reflection or by metallic reflection), the light source then being attached to the guide and interacting with the latter by emitting light into it so that the guide can transmit said light, the one or more light sources emitting into/being coupled to the edge or side face of the guide, for example. This guide is advantageously clear or transparent (i.e., in the case of the guide, having a luminous transmission $T_L$ of at least 30%), and is generally added (joined after having been designed separately) to the lower face of the substrate. It may be organic and/or plastic (for example made of polycarbonate or polymethyl methacrylate PMMA) or mineral, and is preferably mineral; in particular it is glass. The article according to the invention may comprise a number of guides, each dedicated to one or more illuminated regions, or a single guide, containing apertures if required. The guide may be securely fastened to the substrate by adhesive bonding and/or clip-fastening, or by encapsulation, etc. The guide may be joined directly to the substrate or to another part of the article, or to a support on which the article is mounted, for example, in the case of a cooking module or appliance, the guide can be securely fastened to the casing of the cooking appliance on which the substrate is mounted (the casing possibly being part of the article, if required). The guide makes it possible, inter alia, to better transmit the light to the regions that it is desired to illuminate, in particular when the substrate is a dark color.

The article according to the invention may also comprise, in the region to be illuminated, at least one means for extracting the light emitted by the one or more sources, for example one or more scattering elements or treatments, in particular an extracting means such as a layer added to the surface and/or any differential treatment or texturing of the surface (local or over the entire area), of the waveguide if required, such as laser etching, a printed enamel, chemical (acid, etc.) etching, or mechanical roughening (sandblasting, etc.), etc. An extraction area may also be provided, for example, in the bulk of the guide, if required, using, for example, internal laser etching technology. The one or more extraction means make it possible to extract the light from the guide in the region that it is desired to illuminate. If required, the geometry and the roughness of the edge of a waveguide may also be worked on so as to allow local and controlled extraction of the light. The one or more extraction means may be combined, if required, with another treatment allowing the illuminated regions to be targeted, for example a mask (masking certain regions and preventing the light from passing through) screen printed on the substrate.

As defined according to the invention the claimed article also comprises at least one inkjet filter, this filter generally being placed (and in particular occupying a fixed position) between the source and the substrate and possibly being securely fastened (i.e. directly or indirectly (for example by way of another constituent element) fixed and not easily removable once in place) to the source and/or the substrate and/or optionally to another intermediate element (for example a light extraction means such as mentioned above), this intermediate element advantageously being transparent (i.e., in the case of the intermediate element, having a luminous transmission $T_L$ of at least 30%) as will be explained below. Preferably it is securely fastened (or fixed) to the glass-ceramic.

The filter is formed by depositing (or deposited in the form of) at least one layer of ink by inkjet in the chosen location on the substrate and/or on the source and/or on an intermediate element between the substrate and the source in question. The inkjet technique allows (advantageously computer-controlled) deposition of only the amount of ink required, directly, and without contact, on the various types of supports of the article according to the invention, even if they are fragile (another layer). The liquid ink, pulsed through one or more capillary orifices, separates into droplets, each micro-droplet either being electrically or magnetically projected and/or deviated as required on its way to the printing support. The printed image is thus formed from an infinite number of small juxtaposed dots of ink. The printing may be carried out continuously or on demand, the thickness of the final layer (formed by the droplets), corresponding to the inkjet filter obtained, being comprised between 1 μm and 50 μm according to the invention, in order to allow the desired (filter) effect to be obtained while ensuring the filter remains compatible with the manufacturing process of the article according to the invention, especially permitting it to be rapidly and effectively deposited and dried, the inkjet filter obtained preferably being greater than 5 μm and smaller than 30 μm in thickness, and for example being about 10 to 20 μm in thickness.

The composition of the filter is set so that the latter acts on or compensates, in a reproducible, controlled and chosen way, the luminous transmission through the plate (for this purpose, the filter has a spectral dispersion different from that of the glass ceramic). According to the invention, the filter is based on one or more inks, a number of primary-color inks advantageously being superposed in order to form the filter layer. The inks may especially be chosen from various sorts of conventional inks (pigment inks or inks based on soluble dyes, water-based or solvent-based inks, hot-melt inks, photopolymerizable inks (or UV inks), etc.). To prevent nozzle blockage during printing of the filter, the inks are generally polymer inks (or polymer-based inks, which polymer(s) in particular form the medium mentioned below); nevertheless, the ink formulations may include (simultaneously, for example, by way of dyes, or optionally alternatively) other components (metals, ceramics, etc) in particular in the form of nanoparticles, etc. Inks that can be used to obtain the filter according to the invention generally have a composition comprising dyes or pigments (for example making up from 1 to 10%, in particular from 1 to 5% of the weight of the ink), one or more media and/or one or more solvents (for example making up 35 to 90% by weight of the ink), and, if required, one or more additives (such as (a) plasticizer(s), (a) wetting agent(s), (a) surfactant(s), (a) pH or viscosity adjusting agent(s), evaporation-slowing agents, conductors, (a) biocidal agent(s), (an) antifoaming agent(s), (an) antioxidant(s), etc., in amounts that will not generally exceed 15% by weight). The pigments may be mineral or organic pigments, the dyes and/or pigments especially being dissolved or dispersed in the solvent and/or the medium of the ink, the medium, for example, being a silicone, epoxy, polyamide, or acrylic resin, a UV-curable medium, or a sol-gel mineral matrix, the solvent possibly being based on alcohol, methyl ethyl ketone, ethyl acetate, water, etc. Preferably, the one or more inks used are acrylic-based (or formed from an acrylic medium) and, for example, are based on acrylate(s), diacrylate(s), etc. In particular they are inks containing soluble (or dissolved) dyes.

It will be noted that the colored substances, in particular the dyes or pigments, used to produce the aforementioned filters are preferably heat resistant. For example use may advantageously be made, as pigments, of carbon black, phthalocyanine, Lithol Rubine, Diarylide, etc, especially blended, and for example dispersed in a styrene acrylic or phenolic resin. As indicated above, the inks used are in particular UV-curable acrylic (or acrylic medium containing) inks that are temperature and light stable, such as the Anapurna M inks sold by Agfa, for example.

Advantageously, the size of the particles present, if required, in the one or more inks used to obtain the filters according to the invention is smaller than 1 µm, and the viscosity on deposition of the one or more inks is comprised between 5 and 15 mPa·s. Also advantageously, the surface tension of the one or more inks is comprised between 15 and 50 mN/m.

The inkjet filter is generally an absorption filter (this absorption in particular being controlled by the dye or pigments) advantageously allowing the chosen effect or color to be obtained whatever the viewing angle.

The inkjet filter used according to the invention furthermore generally has a luminous transmission of at least 5%, especially of at least 20%, and in particular of at least 30%.

As indicated above, the filter is produced by inkjet printing, in particular on the glass-ceramic substrate and/or the source and/or an intermediate element, and is preferably securely fastened to the glass-ceramic substrate.

If required, the adhesion of the ink to its support, especially when the support is made of a glazing material (the glass-ceramic substrate or source in particular) may be strengthened by a prior treatment (in particular of the support) and/or by adding an appropriate component or additive or composition (for example to the composition of the ink and/or to the surface of the support). In particular, and preferably, the support (or the part of the article required to receive the ink/to which the ink is applied) is treated before the ink is deposited by depositing a chemical adhesion promoter (or tie or primer layer) and/or by carrying out a nonchemical surface treatment (or preparation), especially a plasma treatment (preparation).

In a first embodiment, the surface of the support is prepared/treated beforehand using a plasma treatment (corona or preferably atmospheric plasma treatment).

In a second preferred embodiment of the invention, adhesion of the ink to its support is strengthened by depositing, beforehand, between the ink and its support, at least one tie layer, in particular an appropriate primer layer, and especially a layer based on silane(s) and/or (poly)siloxane(s), as will be described in more detail below. It is also possible to combine the surface preparation plasma treatment and the deposition of the adhesion promoter (for example by applying one or more silanes with a plasma process).

As indicated above, and preferably, at least one tie layer or one layer of an adhesion primer is present between the inkjet filter and the support or the part of the article to which the filter is applied. This primer may especially be applied with a cloth (this cloth being soaked in the primer and wiped over the support, with any eventual excess primer being removed (especially by wiping with another cloth impregnated, for example, with the same solvent as that of the primer), a film of primer being left behind), by roller coating, spray coating, spin coating, curtain coating, screen printing, inkjet printing, or even by plasma processing, etc., coating with a cloth (i.e. the wipe on/wipe off to remove excess technique) generally being simple and effective and in particular being carried out in a way to leave a monomolecular layer (thickness of about one or a few molecules) of primer on the support (the excess, if required, being removed).

The primer is especially and advantageously formed from one or more, in particular functionalized, silane-based compounds (especially a blend of silanes) such as one or more aminosilanes and/or one or more methacrylate silanes (for example 3-(trimethoxysilyl)propyl methacrylate) and/or one or more epoxy silanes, generally dissolved (especially in water or in a solvent such as isopropanol, for example) before application. The primer may thus take the form of a solution of pure silane(s). If required, the primer (especially the aqueous solution of silanes) may also comprise other compounds, and may especially be stabilized by the addition of other compounds (such as organometallic compounds in the case of aminosilanes). The primer may also or alternatively be formed from one or more, in particular functionalized, (poly)siloxane-based compounds.

The thickness of the filter (or of the one or more layers forming the filter), applied (directly, or indirectly with a primer being applied beforehand as indicated above) to at least one part of the article according to the invention, is comprised between 1 and 50 µm as indicated according to the invention, the optional primer generally being about 1 or a few angstroms in thickness (in particular it is a monomolecular layer as mentioned above).

After the one or more inks forming the filter according to the invention have been deposited, the one or more layers of ink may be solidified in various ways depending on the composition of the inks used, for example: at room temperature or by curing and/or heating (thermally, using infrared (IR) radiation, or using ultraviolet (UV) light, etc., high printing speeds and the nature of the support often meaning forced curing is required), this solidification especially taking place via evaporation of the solvents, by polymerization of one of the constituents of the fluid, by oxidation (via oxygen in the air especially), by absorption or penetration into the printing support (often heat activated), by melting, etc. Preferably, this solidification is carried out by polymerizing at least one of the constituents of the ink, for example under ultraviolet radiation.

The choice of the filter specifically appropriate to each case, for obtaining the desired target color (such as perceived by an observer) and/or the desired compensating effect (this being the case, for example, if neutral transmission through the article is desired, the source color being unaltered whatever the source), especially depends on the glass-ceramic plate used, on the desired color (and on the source used in this case) or on the desired effect (the case of neutral transmission, whatever the source) and on the filter used.

In a first embodiment, if it is desired to perfectly compensate transmission through the glass-ceramic so that the glass-ceramic/filter assembly does not alter the color from the source (neutral and constant, or approximately constant transmission, the transmission varying by about 0.5% over the transmission range considered, for example), the required filter primarily depends on the glass-ceramic and must function whatever the light source used. It is then called a universal filter and is capable of correcting the color dispersion introduced by a glass-ceramic (in particular in the form of a plate in the present invention) of a given composition and thickness. The universal filter is selected so that the total optical transmission (transmitted luminous intensity over the incident luminous intensity/luminous intensity emitted by the source) $T_T(\lambda)$ (at each wavelength λ considered, said transmission being measured at normal incidence, or at a more appropriate angle of incidence depending on the chosen conditions of use) through the filter/glass-ceramic assembly is (equal to a) constant over the entire spectral range considered (or for all the wavelengths considered). To do this, the minimum (optical) transmission $T_{Vmin}$ of said glass-ceramic is determined in the spectral range considered, and a filter is sought (or more precisely the composition of the filter, i.e. the relative amounts of the inks, for example cyan, magenta, yellow and black, appropriate to obtain said filter) allowing a constant $T_T(\lambda)$ value to be obtained equal to $T_{Vmin}$ whatever the wavelength in the spectral range considered, the difference $T_T(\lambda)-T_{Vmin}$ preferably not exceeding 0.1, and even more preferably not exceeding 0.01 (in other words $T_T(\lambda)-T_{Vmin}$ is minimized).

Generally, the spectral range considered is the visible spectral range (all the wavelengths lying between 380 nm and 780 nm, especially between 420 and 780 nm). The universal filter chosen allows the source color to be preserved, whatever source is used (the transmission $T_T(\lambda)$ is the same for every wavelength in the visible), only the brightness being altered (brightness obtained for $T_{Vmin}$). Alternatively, the spectral range may be much narrower (for example between 420 and 600 nm) permitting a certain color dispersion (or difference between the color perceived and the color of the source) but maximizing the final perceived brightness, in particular it may be chosen to restrict the spectral range to the range in which the human eye is most sensitive to the electromagnetic radiation received. For example, insofar as the spectral luminous efficiency $V(\lambda)$ (defined by the International Commission on Illumination), modeling the luminous flux perceived by the human eye, reaches its maximum value 1 for a wavelength of 555 nm, the $T_{Vmin}$ value considered may be that measured at about 555 nm, or else, to give another example, insofar as $V(\lambda)$ is greater than 0.5 from 510 nm to 610 nm (for photopic vision, i.e. daytime vision), the $T_{Vmin}$ value considered may be that in the spectral range comprised between 510 nm and 610 nm.

Starting with $T_{Vmin}$, it is therefore possible to deduce the transmission $T_F(\lambda)$ of the desired filter, $T_T(\lambda)$ depending on the transmission of the filter $T_F(\lambda)$ and on that of the glass-ceramic $T_V(\lambda)$ in a ratio that especially depends on the composition of the filter and its thickness (in the simplest case, especially neglecting reflections at the interfaces, $T_T(\lambda)=T_F(\lambda)\times T_V(\lambda)$, to a first approximation). The filter is then produced, for example either empirically in a succession of trials, so as to obtain the desired transmission spectrum $T_F(\lambda)$ (i.e. the spectrum that minimizes $T_T(\lambda)-T_{Vmin}$, for example so that $|T_T(\lambda)-T_{Vmin}|\leq 0,1$), or by numerical/algorithmic etc. optimization of the (filter) variables affecting transmission (for example, pigment concentration, pigment type, filter thickness, etc.), these filter-dependent variables being adjusted during this optimization.

In another embodiment or a variant, when the light source is set or given (the filter then depending, if needs be, on the glass-ceramic and on the source) and it is desired for the color after transmission through the glass-ceramic/filter assembly to be the same as or similar to the initial color of the source, the spectral range considered (in which $T_{Vmin}$ is in particular determined) is the emission range of the source. Alternatively, in the same way as above, a certain color dispersion may be permitted in order to maximize the final brightness perceived, by for example choosing the wavelength(s) (or wavelength interval(s)) in the emission range of the source such that the product $F_e(\lambda)\times V(\lambda)$, normalized to 1 (i.e. for each wavelength $F_e(\lambda)\times V(\lambda)$ is divided by the maximum value of $F_e(\lambda)\times V(\lambda)$ over the emission range of the source, all the values of $F_e(\lambda)\times V(\lambda)$ normalized to 1 then lying between 0 and 1), where $F_e(\lambda)$ denotes, for a given wavelength band, the energy flux spectral density of the source, is greater than 0.1.

In a third embodiment, when the light source is set or given, the filter may be defined so as to obtain a target color that is different to the initial color of the source after transmission through the glass-ceramic/filter assembly. In this case, the calculations are not, as above, based on the value of $T_{Vmin}$ but instead the color coordinates $(x_c, y_c)$ of the desired target color are determined according to the CIE (1931) model and a filter is sought allowing the color coordinates $(x, y)$ associated with the energy flux $T_T(\lambda)\times F_e(\lambda)$ emitted by the source/filter/glass-ceramic assembly to be obtained such that the value $d=((x-x_c)^2+(y-y_c)^2)^{1/2}$ is minimized and in particular is 0.05 or less, preferably 0.01 or less and even more preferably 0.005 or less. If, as is possible, several filters are identified, due to metamerism (identical colors being seen under a given illuminant), the selection may be further refined especially by choosing the solution/filter that gives the highest final luminous flux (for example maximizing $K\times\int TT(\lambda)\times Fe(\lambda)\times V(\lambda)\,d\lambda$ for λ values between 380 and 780 nm, K being a constant equal to 683 lm/W for photopic vision (luminous flux perceived by the eye for a 1 W light source emitting at 555 nm).

Starting with the color coordinates $(x, y)$ thus determined, it is once more possible to deduce the transmission $T_F(\lambda)$ of the desired filter, the formulae of the calculation once more, in particular, being a function of the composition of the filter and its thickness, these parameters being chosen, as above, either empirically in a succession of trials, so as to obtain the desired $T_F(\lambda)$ criteria/transmission spectrum (i.e. the $T_F(\lambda)$ that minimizes the value d), or by numerical/algorithmic etc. optimization of the (filter) variables affecting transmission, these variables, which depend on the filter chosen, being adjusted during this optimization.

Examples of filters are given below. In the case where the inkjet filter according to the invention is formed by depositing a blend of pigments or dyes dispersed in a medium, and if N absorbing species (pigments and/or dyes, for example, and optionally the medium, especially in the case where the latter absorbs a non-negligible amount of light) are blended and then applied to the underside of the glass-ceramic plate, the optimal composition of this colored blend may be identified depending on the desired objective (neutral transmission, same or different color to the initial color of the source) using Beer's law (always applicable in the case considered), which gives the absorbance A for a blend of N absorbent species:

$$A(\lambda) = \sum_{i=1}^{N} \varepsilon_i(\lambda) l C_i$$

where $\varepsilon_i$ is the molar absorptivity of each species, l the length of the optical path through the blend, and $C_i$ the molar concentration of each species. The transmission of the assembly $T_T(\lambda, C_1, \ldots, C_N)$ {mixture of variable composition+glass-ceramic} is then modeled. Depending on the chosen mode (production of a universal filter, or production of a filter for a given glass-ceramic and a given source, with a target color identical to or different from that of the source), it is then possible to seek to optimize $(C_1, \ldots, C_N)$ so that $|T_T(\lambda)-T_{Vmin}|\leq 0.1$, or calculate the color coordinates $(x(C_1, \ldots, C_N), y(C_1, \ldots, C_N))$ associated with the transmitted flux $T_T(\lambda, C_1, \ldots, C_N)F_e(\lambda)$ then to optimize $(C_1, \ldots, C_N)$ so that $d=((x-x_c)^2+(y-y_c)^2)^{1/2}\leq 0.05$, and preferably $\leq 0.01$, as explained above.

The invention also relates to a method for selecting (and/or adjusting) at least one inkjet filter for production of glass-ceramic(s) (glass-ceramic plate(s)) having at least one colored luminous region, in particular a display region, such as explained above, depending on the required objective.

As already mentioned, each inkjet filter is positioned (coupled) with respect to the substrate and the corresponding source in order to correct luminous transmission through the glass-ceramic and is generally positioned (in the illuminated regions) on the lower face of the glass-ceramic. Each filter may be tailored as required depending on the desired goal, as referred to in the above description of selecting methods.

The source/inkjet filter/glass-ceramic combination allows a white or color display to be obtained through the glass-ceramic, which makes it possible to obtain luminous effects that are particularly desirable in design terms. The article according to the invention may thus exhibit one or more luminous/display regions having a functional and/or decorative function (graphic, logo, alphanumeric sign, etc.) generally observed via the main faces (especially the upper face) of the glass-ceramic substrate. Said one or more regions may be located in any region (including heated regions) of the glass-ceramic substrate, and a number of luminous/display regions with different properties (color, luminance levels) may be provided and/or each region may itself display different colors, for example one region may display two colors.

The article according to the invention may, if required, comprise elements and/or layers other than the aforementioned components. For example, when it is a cooking module, the article may be equipped with (or associated with) one or more additional functional or decorative elements (frame, connectors, cables, control elements), etc. It may comprise various functional and/or decorative coatings based on enamel, paint, etc. For example, one of the faces of the substrate may comprise a decorative enamel layer, a masking layer (for example preventing direct observation of the sources), or a layer having another function (for making the illumination more uniform, etc.).

The invention also relates to appliances (or devices) for cooking and/or for maintaining a high temperature comprising at least one article according to the invention (for example, cookers, stoves, ovens, etc) and comprising, if required, one or more heating elements such as one or more radiant or halogen elements and/or one or more gas burners and/or one or more induction heaters. The article according to the invention may also consist of a cooking appliance comprising one or more heating elements other than the elements mentioned above in the definition of the invention. The invention also encompasses cooking appliances comprising a single plate and appliances comprising a number of plates, each of these plates providing, as required, a single ring or multiple rings. The term "ring" is understood to mean a location for cooking. The invention also relates to mixed cooking appliances, the one or more cooktops of which comprise a number of ring types (gas rings, radiant or halogen or induction rings). Furthermore, the invention is not limited to the manufacture of cooking plates or modules for cookers or stoves. The articles manufactured according to the invention may also be other flat modules or plates that need to be largely insensitive to temperature variations.

The cooking appliance, in addition to the internal heating elements, also generally comprises control means and, since the internal elements are covered by the glass-ceramic substrate, the display, in a color other than red, being seen through said substrate, there is provided, if required, on a face or inside of the substrate, at least one masking means intended to mask at least one part of said internal elements.

The present invention also relates to a process for manufacturing an article according to the invention, in which at least one inkjet filter, of thickness comprised between 1 and 50 µm, such as mentioned above according to the invention, and in particular one chosen using the aforementioned selecting method, is integrated, in particular printed, on at least one region of the glass-ceramic substrate and/or the source and/or an intermediate element between the substrate and the source. This filter is especially inserted in the form of a layer deposited on the source or the glass-ceramic substrate, as described above. Advantageously, this filter is inserted after the precursor glass (green glass) has been ceramized, making it possible to obtain the glass-ceramic substrate.

It will be recalled that glass-ceramic plates are generally manufactured as follows: glass having the composition chosen for the glass-ceramic is melted in a melting furnace, then the molten glass is rolled into a standard strip or sheet by passing the molten glass between rollers, and the glass strip is cut to the required dimensions. The plates cut out in this way are then ceramized in a way known per se, the ceramization consisting in annealing the plates with a temperature profile chosen to convert the glass into the polycrystalline material referred to as "glass-ceramic", the thermal expansion coefficient of which is zero or almost zero and which may possibly be able to resist a thermal shock of as much as 700° C. Ceramization generally comprises a gradual increase in temperature until a nucleation domain is reached, which domain is located near the glass-transition domain, a step of crossing the nucleation interval, which takes several minutes, a new gradual increase in temperature to the ceramization plateau temperature, holding the ceramization plateau temperature for several minutes then rapidly cooling the plate to room temperature. Where appropriate, the process also includes a cutting operation (generally before ceramization), for example using a water jet, mechanical scoring using a scoring wheel, etc., followed by a fashioning operation (grinding, beveling, etc.).

The invention also relates to the use of at least one inkjet filter of thickness comprised between 1 and 50 µm (in a luminous device integrated into a glass-ceramic article) to obtain an article having at least one colored luminous region, in particular a display.

Other details and advantageous features will become apparent on reading the description of nonlimiting embodiments of the invention below.

COMPARATIVE EXAMPLE

In this example, the manufactured article was a flat cooking module comprising a glass-ceramic plate (substrate) sold under the trade name KeraVision by Eurokera, this plate having a smooth upper face and a smooth lower face (this face possibly also being provided with bumps) and a thickness of 4 mm, the article furthermore comprising a display unit (light source) comprising white LEDs (7-segment display unit) sold under the reference HDSM-431W by Avago Technologies, and also comprising a combination of two filters chosen from the range of color filters for lighting sold by Lee Filters or by Rosco, the light source being fixed under the plate, and the filters, added below the glass-ceramic plate, being located between the source and the plate. In operation the source emits a light beam that passes through the filters/plate assembly in the display region. The distance between the source and the plate was less than or equal to 5 mm, it may especially be less than 2 mm and even less than 1 mm.

The filters were chosen in the following way: it was desired to obtain, through the plate, a display with a warm white color (target color coordinates $x_c=0.350$, $y_c=0.315$) using a white display unit the initial color coordinates of which were furthermore measured to be ($x_0=0.33\pm0.01$, $y_0=0.29\pm0.01$). Two catalogs of absorption color filters, produced by Lee Filters and Rosco, were available, these filters taking the form of colored (PET) polymer films. It was sought to determine which filter(s) to insert between the display unit and the glass-ceramic plate in order to obtain the target color.

The energy flux density $F_e(\lambda)$ of the source and the spectral optical transmission of the filters and the glass-ceramic were measured (the transmission measurements being carried out on the glass-ceramic plate, the textured face (bumps) of which were removed by polishing if necessary, using an integrating sphere, for example the SPH-12-X model from SphereOptics, coupled to a spectrometer, for example the CAS140 model from Instrument Systems). In particular $(T_T(\lambda))_{i=1\ldots N}$ was evaluated for the N one or more Lee Filters or Rosco color filters it was envisioned would be combined with the glass-ceramic plate, and then the color coordinates $(x_i,y_i)_{i=1\ldots N}$ corresponding to the transmitted flux $(T_T(\lambda)\times F_e(\lambda))_{i=1\ldots N}$ were calculated and all these points $(x_i,y_i)_{i=1\ldots N}$ were plotted in the CIE (1931) color space. The combinations of filters allowing color coordinates (x, y) associated with the energy flux $T_T(\lambda)\times F_e(\lambda)$ emitted by the source/filters/glass-ceramic assembly to be obtained such that the value $d=((x-x_c)^2+(y-y_c)^2)^{1/2}$ is minimized and in particular is 0.05 or less, preferably 0.01 or less, were noted.

It will be noted that the use of only one filter catalog would not allow d to be minimized within fixed limits. In contrast, it was observed that combining two Lee Filters filters, in the case in hand filters 063 and 243, with the given glass-ceramic plate and display unit, allowed the desired target color to be obtained. The value measured for d was 0.002, the luminance obtained, characterizing the visual sensation of brightness, furthermore being 71 cd/m$^2$. The white light obtained through the article has the following color coordinates x=0.348, y=0.314.

Thermal tests were furthermore carried out after the filters had been inserted between the plate and the source, a hot saucepan being transferred plumb with the filters. This saucepan was heated to bring water to the boil (leading to a temperature on the lower face of the glass-ceramic, after transfer, of about 60° C.), to cook fries (leading to a temperature on the lower face of the glass-ceramic, after transfer, of about 85° C.) or an empty saucepan was heated (leading to a temperature on the lower face of the glass-ceramic, after transfer, of about 200° C.).

The filters placed in contact with the glass-ceramic were deformed after transfer of the hot saucepan in each of these cases. After the glass-ceramic plate and the filters had been separated by a distance of 1 mm, deformation was only observed when the empty hot saucepan was transferred. After the glass-ceramic plate and the filters had been separated by a distance of 2.5 mm, no deformation was observed.

Example according to the invention:

In this example, it was sought to produce a filter having an appropriate absorption, so as to obtain the white rendering sought above with the plate and display unit mentioned in the comparative example, by inkjet printing it, according to the invention, on the glass-ceramic substrate. The inks used were UV-curable acrylic inks, which were temperature and light stable, chosen from the Anapurna M inks sold by Agfa, for example. The lower face of the glass-ceramic, in the display region above the source, was coated beforehand, using a cloth, with a monomolecular layer of a primer taking the form of an aqueous solution of aminosilanes stabilized with organometallic compounds (sold under the reference Hydropep 100 by Sika France). A database was available containing the spectra of the filters resulting from possible blends of the, especially primary, colors (in particular cyan/magenta/yellow/black) used. For each filter in the color database, the color point (x,y) of the source seen through the plate plus filter assembly was determined, and the filter allowing color coordinates (x, y) associated with the energy flux $T_T(\lambda)\times F_e(\lambda)$ emitted by the source/filters/glass-ceramic assembly to be obtained such that the value $d=((x-x_c)^2+(y-y_c)^2)^{1/2}$ is minimized and in particular is 0.05 or less, preferably 0.01 or less and even more preferably 0.005 or less, was selected.

The filter thus selected was printed, with a thickness of about 10 μm, by inkjet printing on the aforementioned primer layer on the lower face of the glass-ceramic (for example using an Anapurna M printer with an at least 4-pass printing configuration), the filter resulting from blending the colors of the printer. Thus the filter selected, in the present example, in order to obtain the desired white color, resulted from a blend of 76% (quantity relative to the maximum quantity of this color deliverable by the printer) Anapurna M (trademark) primary color cyan ink sold by Agfa, and 34% (relative to the maximum quantity of this color deliverable by the printer) Anapurna M (trademark) primary color yellow ink sold by Agfa, these inks being based on diacrylate oxybis(methyl-2,1-ethanediyl), isodecyl acrylate and acrylate ester.

The value measured for d was 0.000, the luminance obtained, characterizing the visual sensation of brightness, furthermore being 109 cd/m$^2$, this luminance being better than that obtained with the polymer filters. The white color obtained through the article had the following color coordinates x=0.350, y=0.315 corresponding to the white color sought.

The same thermal tests as those carried out in the comparative example were furthermore carried out on the article equipped with the inkjet filter of thickness of about 10 μm thus obtained, via transfer, plumb with the filter, of a hot saucepan. No deformation or optical effects were observed in any of the tests. A better thermal withstand was therefore observed for the article according to the invention than was the case for the polymer filters used according to the comparative example. Thus, the solution according to the invention uses compositions that are thermally resistant at all the temperatures to which the control panel is exposed, whether in an inductive or radiant application, which is not the case for a solution employing polymer filters, the filter having to be separated from the glass ceramic by at least 1 mm in the latter case, making it more difficult to implement the filter.

The articles, in particular plates, according to the invention may in particular be advantageously used to produce a new range of cooktops for cookers or ranges, but may also be advantageously used to produce wall elements or walls (for example doors or parts of doors) of ovens, etc.

The invention claimed is:

1. An article having at least one colored luminous region said article comprising:
   at least one glass-ceramic substrate having a luminous transmission ranging from 0.8% to 40% and an optical transmission of at least 0.1% for at least one wavelength in the range extending from 420 to 780 nm;
   at least one light source; and
   at least one inkjet filter of thickness between 1 and 50 μm, so as to form at least one colored luminous region in at least one region of the glass-ceramic substrate.

2. The article as claimed in claim 1, wherein the filter is a color filter obtained by superposing depositions of a number of colors.

3. The article of claim 2, wherein the colors are primary colors.

4. The article as claimed in claim 1, wherein the filter is a color filter defined by a ratio of colors.

5. The article as claimed in claim 1, wherein the filter is obtained from one or more inks, each ink comprising:
   at least one medium and/or one solvent;
   at least one dye or pigment; and
   optionally one or more additives.

6. The article as claimed in claim 5, wherein:
   a size of particles present in the one or more inks is smaller than 1 μm;
   a viscosity on deposition of the one or more inks is between 5 and 15 mPa·s; and
   a surface tension of the one or more inks is between 15 and 50 mN/m.

7. The article of claim 5, wherein at least one ink comprises a UV curable acrylic medium.

8. The article as claimed in claim 1, wherein the filter has a luminous transmission of at least 5%.

9. The article as claimed in claim 1, wherein the inkjet filter is applied or printed onto at least one of the glass-ceramic substrate, the light source, and an intermediate element.

10. The article as claimed in claim 9, wherein the at least one of the glass ceramic substrate, the light source and the intermediate element to which the filter is applied is treated before the ink is deposited by depositing an adhesion promoter, by carrying out a nonchemical surface treatment, or both.

11. The article as claimed in claim 10, wherein at least one tie layer or primer adhesion layer is present between the inkjet filter and the at least one of the glass ceramic substrate, the light source and the intermediate element to which the filter is applied.

12. The article of claim 10, wherein the at least one of the glass ceramic substrate, the light source and the intermediate element to which the filter is applied is treated by a plasma treatment.

13. The article as claimed in claim 10, wherein at least one tie layer or primer adhesion layer based on at least one silane selected from the group consisting an aminosilane, a methacrylate silane, an epoxy silane and a (poly)siloxane, is present between the inkjet filter and the at least one of the glass ceramic substrate, the light source and the intermediate element part of the article to which the filter is applied.

14. The article as claimed in claim 1, wherein the filter is chosen depending on the glass-ceramic, so as to form at least one luminous region having a color other than red.

15. The article as claimed in claim 1, wherein the filter is a filter that compensates the transmission of the glass-ceramic so that a resulting glass-ceramic/filter assembly has a total optical transmission that is approximately constant in a preselected spectral range.

16. The article as claimed in claim 1, wherein the article comprises one or more filters to obtain a target color that is selected to be identical to or different from an initial color of the source.

17. The article as claimed in claim 1, further comprising one or more heating elements.

18. A method for producing the article of claim 1, the method comprising selecting the at least one inkjet filter by:
   determining a minimum transmission $T_{Vmin}$ of a glass-ceramic in a selected spectral range; and
   selecting a filter allowing a constant total transmission value $T_T(\lambda)$ for a resulting glass-ceramic/filter assembly equal to $T_{vmin}$ at a wavelength in the spectral range, wherein a difference $T_T(\lambda)-T_{Vmin}$ is less than or equal to 0.1.

19. A method for producing the article of claim 1, the method comprising:
   determining color coordinates $(x_c, y_c)$ of a desired target color; and
   selecting a filter allowing color coordinates $(x, y)$ associated with an energy flux $T_T(\lambda) \times F_e(\lambda)$ emitted by a source/filter/glass-ceramic assembly of the article such that a value $d=((x-x_c)^2+(y-y_c)^2)^{1/2}$ is less than or equal to 0.05.

20. A process for manufacturing the article of claim 1, the process comprising integrating at least one inkjet filter having a thickness of between 1 and 50 μm on at least one region of a glass-ceramic substrate, a light source, an intermediate element between the substrate and the light source, or a combination thereof,
   wherein:
   the at least one inkjet filter is selected by
      (i) determining a minimum transmission $T_{Vmin}$ of a glass-ceramic in a selected spectral range, and
      (ii) selecting a filter allowing a constant total transmission value $T_T(\lambda)$ for a resulting glass-ceramic/filter assembly equal to $T_{vmin}$ at a wavelength in the spectral range,
      wherein a difference $T_T(\lambda)-T_{Vmin}$ is less than or equal to 0.1; or
   the at least one inkjet filter is selected by
      (i) determining color coordinates $(x_c, y_c)$ of a desired target color, and
      (ii) selecting a filter allowing color coordinates $(x, y)$ associated with an energy flux $T_T(\lambda) \times F_e(\lambda)$ emitted by a source/filter/glass-ceramic assembly of the article such that a value $d=((x-x_c)^2+(y-y_c)^2)^{1/2}$ is less than or equal to 0.05.

21. The article of claim 1, wherein the colored luminous region is a display.

22. The article as claimed in claim 1, wherein the filter is obtained from one or more inks, each ink comprising:
   at least one medium, one solvent, or both, in amounts of 35 to 90% by weight;
   at least one dye or pigment in amounts of 1 to 10% by weight; and
   optionally one or more additives in amounts of 0 to 15% by weight.

23. The article as claimed in claim 1, wherein the filter is chosen depending on the glass-ceramic, so as to form at least one luminous region having a color other than red and in a colored region having at least one of a white color and a synthetic color obtained by mixing a number of wavelengths.

* * * * *